US006984400B2

(12) United States Patent
Golomb et al.

(10) Patent No.: US 6,984,400 B2
(45) Date of Patent: *Jan. 10, 2006

(54) METHOD OF TREATING RESTENOSIS USING BISPHOSPHONATE NANOPARTICLES

(75) Inventors: Gershon Golomb, Efrat (IL); Haim Danenberg, Brookline, MA (US)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 19 days.

This patent is subject to a terminal disclaimer.

(21) Appl. No.: 10/126,248

(22) Filed: Apr. 19, 2002

(65) Prior Publication Data

US 2002/0187184 A1 Dec. 12, 2002

Related U.S. Application Data

(63) Continuation-in-part of application No. 09/743,705, filed as application No. PCT/IL99/00387 on Jul. 14, 1999, now Pat. No. 6,719,998.

(30) Foreign Application Priority Data

Jul. 14, 1998 (IL) ................................................ 125336

(51) Int. Cl.
    *A61K 9/14*     (2006.01)
    *A61K 9/127*    (2006.01)
    *A01N 57/00*    (2006.01)

(52) U.S. Cl. .................... 424/489; 424/450; 514/75; 514/102; 514/824; 514/951

(58) Field of Classification Search ................ 424/400, 424/422, 423, 450, 484, 489, 490; 514/102, 514/103, 104, 106, 107, 108, 937
See application file for complete search history.

(56) References Cited

U.S. PATENT DOCUMENTS

| 4,067,971 A | 1/1978 | Francis et al. |
| 4,216,211 A | 8/1980 | Francis |

(Continued)

FOREIGN PATENT DOCUMENTS

| DE | 196 37 890 A1 | 3/1998 |
| EP | 0 339 237 | 11/1989 |

(Continued)

OTHER PUBLICATIONS

Patashnik et al, J. Drug Target, Preparation and Evaluation of chitosan microspheres containing bisphosphonates, 1997, 4(6):371–80).*

(Continued)

*Primary Examiner*—Gary Kunz
*Assistant Examiner*—Sharmila S. Gollamudi
(74) *Attorney, Agent, or Firm*—Morgan & Finnegan, LLP

(57) ABSTRACT

A method of treating or preventing restenosis by administering to an individual an effective amount of an active ingredient comprising a bisphosphonate particle or a bisphosphonate particulate. The bisphosphonate may be encapsulated, embedded or adsorbed within the particle, dispersed uniformly in the polymer matrix, adsorbed on the particle surface, or in combination of any of these forms. The particles include liposomes or inert polymeric particles, such as microcapsules, nanocapsules, nanoparticles, nanospheres, or microparticles. The particulates include any suspended or dispersed form of the bisphosphonate which is not encapsulated, entrapped, or adsorbed within a polymeric particle. The particulates include suspended or dispersed colloids, aggregates, flocculates, insoluble salts and insoluble complexes of the active ingredient. The active ingredient effects restenosis by inhibiting the growth and proliferation of the cell types involved in the restenotic cascade, such as macrophages/monocytes, fibroblasts and smooth-muscle cells.

14 Claims, 10 Drawing Sheets

U.S. PATENT DOCUMENTS

| | | | |
|---|---|---|---|
| 5,096,717 A | | 3/1992 | Wirth et al. |
| 5,196,409 A | | 3/1993 | Breuer et al. |
| 5,312,954 A | | 5/1994 | Breuer et al. |
| 5,338,731 A | | 8/1994 | Breuer et al. |
| 5,492,926 A | * | 2/1996 | Cullinan et al. ............ 514/422 |
| 5,652,227 A | | 7/1997 | Teronen et al. |
| 5,733,564 A | | 3/1998 | Lehtinen |
| 5,741,514 A | | 4/1998 | Barenholtz et al. |
| 5,760,030 A | | 6/1998 | Bryant et al. |
| 5,776,429 A | * | 7/1998 | Unger et al. ............... 424/9.52 |
| 5,792,885 A | | 8/1998 | Ham et al. |
| 5,882,656 A | | 3/1999 | Bechard et al. |
| 5,932,563 A | | 8/1999 | Stokes et al. |
| 5,932,580 A | | 8/1999 | Levitzki et al. |
| 5,994,341 A | | 11/1999 | Hunter et al. |
| 6,139,871 A | | 10/2000 | Hope et al. |
| 2002/0192157 A1 | | 12/2002 | Low et al. |

FOREIGN PATENT DOCUMENTS

| | | | |
|---|---|---|---|
| EP | 0459 318 | | 12/1991 |
| WO | 97 33552 | | 9/1997 |
| WO | WO 97/43437 | * | 11/1997 |
| WO | WO 88 00289 | | 2/1998 |
| WO | 98 31359 | | 7/1998 |
| WO | 99 38998 | | 8/1999 |
| WO | 00 21540 | | 10/1999 |
| WO | 00 34293 | | 6/2000 |
| WO | 00 64516 | | 11/2000 |

OTHER PUBLICATIONS

Monkkonen et al, Calcif Tissue Int., vol. 53, 1993.*
Makkar et al (J. Cardiovascular Pharmacology Therapy, Apr. 1996, 1(2): 177–188).*
Rubin et al., "Cellular and Molecular Mechanisims of Radiation Inhibition of Restenosis. Part I: Role of the Macrophage and Platelet–Derived Growth Factor", *Int. J. Radiation Oncology Biol. Phys.* (1998), vol. 40, pp. 929–941.
Monkkonen et al., "Studies on Liposome Formulations for Intra–articular Delivery of Clodronate", *Journal of Controlled Release,* (1995), vol. 35, pp. 145–154.
Abstract, Kunitomo et al., "Experimental Induction of Athero Sclerosis in Guinea–Pigs Fed a Cholesterol Vitamin D–2–Rich Diet", (1983).
Mönkkönen et al., "The Effect of Liposome–Encapsulated and free Clodronate on the Growth of Macrophage–like Cells In Vitro: The Role of Calcium and Iron", *Calcif. Tissue International,* (1993), vol. 53, pp. 139–146.
Gennaro, "Parenteral Preparations", *Remington: The Science and Practice of Pharmacy,* 20$^{th}$ Edition, Chapter 41, pp. 780–920.
Kramsch et al., "Th effect of Agents Interfering with Soft Tissue Calcification and Cell Proliferation on Calcific Fibrous–Fatty Plaques in Rabbits", *Circulation Research,* (1978), vol. 42, No. 4, pp. 562–570.
Mönkkönen et al., "Growth Inhibitions of Macrophage–Like and Other Cell Types by Liposome–Encapsulated, Calcium–Bound, and Free Bisphosphonates In Vitro", *Journal of Drug Targeting,* (1994), vol. 2, pp. 299–308.
Fleisch, "Bisphosphonates in bone disease" *Parthenon Publishing Group Inc.,* (1997), pp. 184–210.
Mak et al., "Clinical Trials to prevent Restenosis after Precutaneous Coronary Revescularization", *The NY Academy of Sciences,* (1994), pp. 225–277.

LeClerc et al., "Drug prevention of restenosis after angioplasty: an update", *Elsevier Science,* (1995), pp. 722–724.
Lefkovits et al., "Pharmacological Approaches for the Prevention of Restenosis After Percutaneous Coronary Intervention", *Progress in Cardiovascular Disease,* (1997), vol. 40, No. 2, pp. 141–158.
Hamon et al., "Restenosis after coronary angioplasty", *European Heat Journal,* (1995), vol. 16, pp. 33–48.
Gottsauner–Wolf et al., "Influence of local delivery of the protein tyrosine kinase receptor inhibitor tyrphostin–47 on smooth–muscle cell proliferation in rat carotid balloon–injury model", *American Heart Journal,* (1996), vol. 19, pp. 347–356.
Donbrow, "Microcapsules and Nanoparticles In Medicine and Pharmacy", CRC Press, Boca Raton, Fl. pp. 347.
Shioi et al., "β–Glycerophoshate Accelerates Calcification in Cultured Bovine Vascular Smooth Muscle Cells", *Arteriosclerosis, Thrombosis and Vascular Biology,* (1995), vol. 15, No. 11, pp. 2003–2009.
Paspaliaris et al., "Clodronate Inhibits Contraction and prevents the Action of L–Type Calcium Channel Antagonists in Vascular Smooth Muscle", (1991), *Journal of Bone and Mineral Research,* vol. 6, No. 8, pp. 835–841.
Bellah et al., "Idiopathic arterial calcification of Infancy: Prenatal and postnatal effects of therapy in an infant", (1992), *The Journal of Pediatrics,* vol. 121, No. 6, pp. 930–933.
Waller et al., "Coronary Artery and Saphenous Vein Graft Remodeling: A Review of Histologic Findings after Various Interventional Procedure—Part VI", *Clin Cardiol.,* (1997), vol. 20, pp. 153–160.
Anderson et al., "A review of randomized trials comparing coronary angioplasty and bypass grafting", *Curr–Opin–Cardiol,* (1996), vol. 11, No. 6, pp. 583–590.
Moorman et al., "Percutaneous Transluminal Coronary Angioplasty (PTCA): Long–term Outcome and Aeromedical Implications", *Aviation, Space and Environmental Medicine,* (1996), vol. 67, No.10, pp. 990–996.
Laurent et al., "The arterial wall: a new pharmacological and therapeutic target", *Fundam Clin Phramacol,* (1996), vol. 10, pp. 243–257.
Schwartz, "The vessel wall reaction in restenosis", *Semin–Interv–Cardiol,* (1997), vol. 2, pp. 83–88.
Allaire et al, "Endothelial Cell Injury in Cardiovascular Surgery: The Intimal Hyperplastic Response", *Ann Thorac Surg,* (1997), vol. 63, pp. 582–591.
Webb et al, "Inhibition of Bioprosthetic Heart Valve Calcification with Aminodiphosphonate Covalently Bound to Residual Aldehyde Groups", *Ann Thorac Surg.,* (1988), vol. 46, pp. 309–316.
Wagner et al., "Contrasting Effects of Ethane–1–Hydroxy–1, 1–Diphosphonate (EHDP) on the Regression of two types of Dietary–Induced Atherosclerosis", *Atherosclerosis,* (1977), vol. 27, pp. 419–435.
Daoud et al., "The effect of ethane–1–hydroxy–1, 1–diphosphonate (EHDP) on necorsis of atherosclerotic lesions", *Atherosclerosis,* (1987), vol. 67, pp. 41–48.
Walsh et al., "Molecular strategies to inhibit restenosis: modulation of the vascular myocyte phenotype", *Semin Intervent Cardiol,* (1996), vol. 1, pp. 173–179.
Hermann et al., "Pharmacological Approaches to the prevention of Restenosis Following Angioplasty", *Drug,* (1993), vol. 46, No. 1, pp. 18–52.

Ylitalo, 2002, "Bisphosphonates and atherosclerosis" *General Pharmacology* 35:287–296.

Kramsch et al., "The Effect of Agents Interfering with Soft Tissue Calcification and Cell Proliferation on Calcific Fibrous–Fatty Plaques in Rabbits", Circulation Research, (1978), vol. 42, No. 4, pp. 562–570.

Fleisch, "Bisphophonates in bone disease", Parthenon Publishing Group Inc., (1997), pp. 184–210.

Mak, et al., "Clinical Trials to Prevent Restenosis after Percutaneous Coronary Revescularization", The NY Academy of Sciences, (1994), pp. 225–277.

Lefkovtis et al., "Pharmacological Approaches for the Prevention of Restenosis After Percutaneous Coronary Intervention", Progress in Cardiovascular Disease, (1997), vol. 40, No. 2, pp. 141–158.

Hamon et al., "Restenosis after Coronary Angioplasty", European Heat Journal, (1995), vol. 16, pp. 33–48.

Shioi et al., "β–Glycerophosphate Accelerates Calcification in Cultured Bovine Vascular Smoth Muscle Cells", *Arteriosclerosis, Thrombosis and Vascular Biology*, (1995), vol. 15, No. 11, pp. 2003–2009.

Allaire et al., "Endothelial Cell Injury in Cardiovascular Surgery: The Intimal Hyperplastic Response", *Ann Thorac Surg,* (1997), vol. 63, pp. 582–591.

Webb et al., "Inhibition of Bioprosthetic Heart Valve Calcification with Aminodiphosphonate Covalently Bound to Residual Aldehyde Groups", *Ann Thorac Surg.,* (1988), vol. 46, pp. 309–316.

Walsh et al., "Molecular Strategies to Inhibit Testenosis: Modulation of the Vacular Myocyte Phenotype", *Semin Intervent Cardiol,* (1996), vol. 1, pp. 173–179.

Rubin et al., "Cellular and Molecular Mechanisms of Radiation Inhibition of Restenosis. Part I: Role of the Macrophage and Platelet–Derived Growth Factor", *Int. J. Radiation Oncology Biol. Phys.* (1998), vol. 40, pp. 929–941.

* cited by examiner

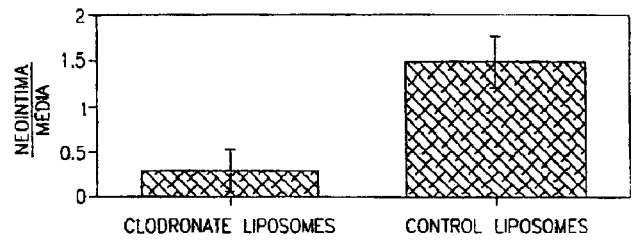
FIG.1
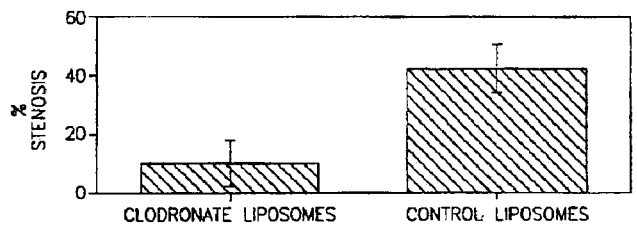
FIG.2
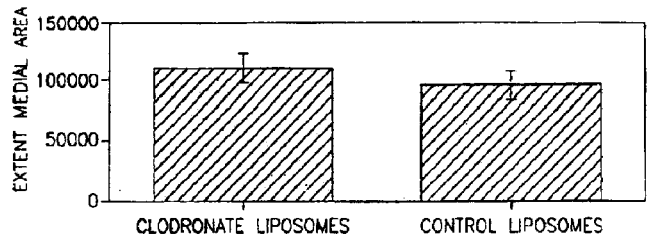
FIG.3
| Treatment type | Animal (No.) | Dosing days | N/M | % stenosis |
|---|---|---|---|---|
| Empty liposomes | Rat (20) | -1, +6 | 1.62 ± 0.1 | 44.5 ± 2.0 |
| Clodronate | Rat (10) | -1, +6 | 1.2 ± 0.2 | 40.2 ± 7.2 |
| Liposomal clodronate 15 mg/kg | Rat (10) | -1 | 0.45 ± 0.1 | 15.4 ± 3.4 |
| Liposomal clodronate 15 mg/kg | Rat (10) | -1, + 6 | 0.35 ± 0.07 | 12.0 ± 2.3 |
| Empty liposomes | Rabbit (10) | -1 | 1.94 ± 0.3 | 86.6 ± 4.0 |
| Liposomal clodronate 10 mg/kg | Rabbit (10) | -1 | 1.11 ± 0.2 | 71.5 ± 2.1 |
| Silica particles 1000 mg/kg | Rat (10) | -1 | 0.8 ± 0.1 | 24.2 ± 3.8 |
FIG. 4

|  | | Blank NP (N=12) | ISA NP (N=15) |
|---|---|---|---|
| Size (nm) | Before lyophilization | 349±158 | 376±55 |
|  | After lyophilization | 402±189 | 396±70 |
| Recovery (%) Final Wt./Initial Wt. | | 63.8±10.9 | 68.7±8.7 |
| ISA entrapment (% of initial) | | | 59.6±6.1 |
| Final ISA content (%) (ISA weight/NP total weight) | | | 16.5±2.7 |
| ISA in NP (mg) | | | 11.9±2.0 |
| ISA in supernatant (mg) | | | 1.1±0.45 |
| Initial ISA content (%) | | | 18.1 |
| $Ca^{2+}$ recovery (%) | | 88.3±10.9 (N=8) | 72.3±11.9 (N=8) |
| $Ca^{2+}$ in supernatant (%) | | 88 | 38 |
| $Ca^{+2}$ in NP (%) | | 0 | 34 |
| $Ca^{2+}$/ISA (mol) | | | 1.2±0.3 |
| Zeta potential (mV) | | -6.2±1.8 | -5.7±0.9 |

FIG. 5

| Formulation parameters | Alendronate NP (n=7) |
|---|---|
| Size (nm) | 219±10 |
| Alendronate entrapment (% of initial) | 55.09±7.40 |
| Alendronate in NP (mg/ml) | 1.002±0.135 |
| Alendronate in supernatant (mg/ml) | 0.232±0.138 |
| Initial amount of alendronate (mg) | 20 |
| PLGA amount (mg) | 90 |
| Volume of calcium chloride 0.246M (ml) | 0.5 |

FIG. 9

| Effect of Alendronate NP on RAW264 proliferation | |
|---|---|
| Concentration (μm) | % Inhibition (vs. control) |
| 1 | 3.60±1.3 |
| 5 | 13.53±4.24 |
| 10 | 25.73±12.33 |
| 50 | 98.14±0.04 |

FIG. 10

METHOD OF TREATING RESTENOSIS USING BISPHOSPHONATE NANOPARTICLES

This application is a continuation-in-part of application Ser. No. 09/743,705 filed on Mar. 22, 2001, now U.S. Pat. No. 6,719,998, which is a 35 U.S.C §371 filing of PCT application no. PCT/IL99/00387 filed on Jul. 14, 1999, which is a continuation-in-part of Israeli application no. 125336 filed on Jul. 14, 1998.

FIELD OF THE INVENTION

The present invention is concerned with compositions capable of preventing, inhibiting or reducing restenosis (sometimes referred to in the art as "accelerated arteriosclerosis" and "post-angioplasty narrowing"). Specifically, the invention relates to the use of bisphosphonate ("BP") nanoparticles ("NP") to effectively treat restenosis.

BACKGROUND OF THE INVENTION

Over the past decade, mechanical means of achieving revascularization of obstructive atherosclerotic vessels have been greatly improved. Percutaneous transluminal coronary angioplasty (PTCA) procedures include, but are not limited to, balloon dilatation, excisional atherectomy, endoluminal stenting, rotablation and laser ablation. However, revascularization induces thrombosis, and neointimal hyperplasia, which in turn cause restenosis in a substantial proportion of coronary arteries after successful balloon angioplasty and in aortacoronary saphenous vein bypass graft and other coronary grafts. Furthermore, intimal hyperplasia causes restenosis in many superficial femoral angioplasties, carotid endarterectomies, and femoro-distal vein bypasses. Restenosis is the formation of new blockages at the site of the angioplasty or stent placement or the anastomosis of the bypass. As a result, the patient is placed at risk of a variety of complications, including heart attack or other ischemic disease, pulmonary embolism, and stroke. Thus, such procedures can entail the risk of precisely the problems that its use was intended to ameliorate. The introduction of endovascular stents has reduced the incidence of restenosis, but this problem still remains significant, since restenosis or "over exuberant" tissue healing may occur at the site of stent placement. (Waller, B. F. et al., 1997, *Clin-Cardiol.,* 20(2):153–60; Anderson, W. D et al., 1996, *Curr-Opin-Cardiol.,* 11(6):583–90; Moorman, D. L. et al., 1996, *Aviat-Space-Environ-Med.,* 67(10):990–6; Laurent, S. et al., 1996, *Fundam. Clin. Phamacol.* 10(3):243–57; Walsh, K. et al., 1996, *Semin-Interv-Cardiol.,* 1(3):173–9; Schwartz, R. S., 1997, *Semin-Interv-Cardiol.,* 2(2):83–8; Allaire, E. et al., 1997, *Ann. Thorac. Surg.,* 63:582–591; Hamon, M. et al., 1995, *Eur. Heart J.,* 16:33s–48s; Gottsauner-Wolf, M., et al., 1996, *Clin. Cardiol.,* 19:347–356).

Despite extensive research on the incidence, timing, mechanisms and pharmacological interventions in humans and animal models to date, no therapy exists which consistently prevents coronary restenosis (Herrman, J. P. R. et al., 1993, *Drugs,* 46:18–52; Leclerc, G. et al., 1995, *Elsevier Science,* 722–724, Topol, E., 1997, *The NY Academy of Sciences,* 225–277). Compositions and methods for the reduction or prevention of restenosis are still greatly desired. Accordingly, it would be desirable to develop novel compositions and methods that are effective in treating restenosis and preventing its reoccurrence.

Bisphosphonates ("BPs") (formerly called diphosphonates) are compounds characterized by two C—P bonds. If the two bonds are located on the same carbon atom (P—C—P) they are termed geminal bisphosphonates. The BPs are analogs of the endogenous inorganic pyrophosphate which is involved in the regulation of bone formation and resorption. The term bisphosphonates is generally used for geminal and non-geminal bisphosphonates. The BPs may at times form polymeric chains. BPs act on bone because of their affinity for bone mineral and also because they are potent inhibitors of bone resorption and ectopic calcification. BPs have been clinically used mainly as (a) antiosteolytic agents in patients with increased bone destruction, especially Paget's disease, tumor bone disease and osteoporosis; (b) skeletal markers for diagnostic purposes (linked to $^{99m}Tc$); (c) inhibitors of calcification in patients with ectopic calcification and ossification, and (d) antitartar agents added to toothpaste (Fleisch, H., 1997, in: Bisphosphonates in bone disease. Parthenon Publishing Group Inc., 184–186). Furthermore, being highly hydrophilic and negatively charged, BPs in their free form are almost incapable of crossing cellular membranes.

SUMMARY OF THE INVENTION

In one embodiment, the present invention relates to a method of treating or preventing restenosis by administering to an individual an effective amount of an active ingredient comprising a bisphosphonate, a bisphosphonate salt, a bisphosphonate ester, or a bisphosphonate complex, wherein the active ingredient is in a particle dosage form.

In a further embodiment, the present invention relates to a method of treating or preventing restenosis by administering to an individual an effective amount of an active ingredient comprising a bisphosphonate, an insoluble bisphosphonate salt, an insoluble bisphosphonate ester, or an insoluble bisphosphonate complex, wherein the active ingredient is in a free particulate dosage form.

In a "particle" dosage form, the active ingredient may be encapsulated, entrapped, embedded, or adsorbed within the particle, dispersed in the polymer matrix, adsorbed or linked on the particle surface, or in combination of any of these forms. The particles include, but are not limited to, inert polymeric particles, such as microcapsules, nanocapsules, nanospheres, microspheres, nanoparticles, microparticles, or liposomes. In a "free particulate" dosage form, the active ingredient includes any suspended or dispersed particulate form of the active ingredient itself which is not encapsulated, entrapped or adsorbed within a polymeric particle. Free particulates include, but are not limited to, colloids, aggregates, flocculates, insoluble salts, and insoluble complexes. Additionally, in both the particle and free particulate dosage forms, suspending agents and stabilizers may be used. Effective phagocytosis of both the bisphosphonate particles and the bisphosphonate free particulates by the monocytes/macrophages can affect the activity of such phagocytic cells. The active ingredient affects restenosis by inhibiting phagocytic cells involved in the restenotic cascade, such as macrophages/monocytes and fibroblasts. The delivery system affects smooth-muscle cells (SMC) and extracellular matrix production indirectly by inhibiting the cells that trigger their migration and/or proliferation. Nevertheless, a direct effect on SMC may also occur. The active ingredient may be administered by any route which effectively transports the active compound to the desirable site of action. In a preferred embodiment, the mode of administration includes intra-arterial, intravenous or subcutaneous administration.

In a further embodiment, the present invention includes a method of treating or preventing restenosis by administering to an individual, an effective amount of any compound or composite known to inactivate or inhibit blood monocytes and tissue macrophages, thereby treating or preventing restenosis.

In a further embodiment, the present invention includes a pharmaceutical composition comprising an active ingredient selected from the group consisting of a bisphosphonate particle, a bisphosphonate particulate, or a salt, ester, or complex of bisphosphonate, together with a pharmaceutically acceptable carrier, stabilizer or diluent for the prevention or treatment of vascular restenosis.

BRIEF DESCRIPTION OF THE DRAWINGS

FIGS. 1–3 are bar graphs of results demonstrating the effect of clodronate encapsulated in liposomes on the reduction of restenosis in an experimental rat carotid catheter injury model as compared to the effect of control liposomes which did not contain clodronate on the same rats. In these figures:

FIG. 1 shows the mean neointimal area to the area of the media in rats treated with clodronate containing liposomes as compared to rats treated with control liposomes. The medial area is the difference between the total arterial area and the original lumen area.

FIG. 2 shows the % stenosis in rats treated with clodronate containing liposomes as compared to the % stenosis in rats treated with control liposomes.

FIG. 3 shows the extent of medial area as an indirect index of smooth muscle cell viability and determined as the difference between the total arterial area and the original lumen area (External elastic lamina bound area—Internal elastic lamina bound area) in rats treated with clodronate containing liposomes as compared to rats treated with control liposomes only.

FIG. 4 illustrates the antirestenotic effects of liposomal clodronate in the balloon-injured rat and atherosclerotic rabbit carotid arterial models.

FIG. 5 tabulates the characteristics of a typical formulation of ISA encapsulated nanoparticles.

FIG. 8a illustrates the % stenosis in rats treated with ISA encapsulated nanoparticles as compared to the % stenosis in rats treated with control nanoparticles; and FIG. 8b illustrates the mean neointimal area to the area of the media ratio in rats treated with ISA encapsulated in nanoparticles as compared to rats treated with control nanoparticles. The medial area is the difference between the total arterial area and the original lumen area.

FIG. 9 tabulates the characteristics of a typical formulation of alendronate encapsulated in nanoparticles.

FIG. 10 tabulates the effect of alendronate loaded nanoparticles on the proliferation of RAW 264 cells.

FIG. 11 illustrates the % stenosis in rats treated with alendronate loaded nanoparticles as compared to the % stenosis in rats treated with control nanoparticles, wherein the particles were administered subcutaneously;

FIG. 12a compares the % stenosis in rats treated with: 1.5 mg/kg of alendronate loaded nanoparticles via SC administration, 0.15 mg/kg of alendronate loaded nanoparticles via SC administration and 0.15 mg/kg of alendronate loaded nanoparticles via IV administration; and FIG. 12b illustrates the mean neointimal to medial area ratio (N/M) in rats treated with ISA loaded nanoparticles as compared to rats treated with control nanoparticles, and also compares the mean neointimal area to medial area ratio (N/M) in rats treated with: 1.5 mg/kg of alendronate loaded nanoparticles via SC administration, 0.15 mg/kg of alendronate loaded nanoparticles via SC administration and 0.15 mg/kg of alendronate loaded nanoparticles via IV administration. The medial area is the difference between the total arterial area and the original lumen area.

DETAILED DESCRIPTION OF THE INVENTION

Figure 6:
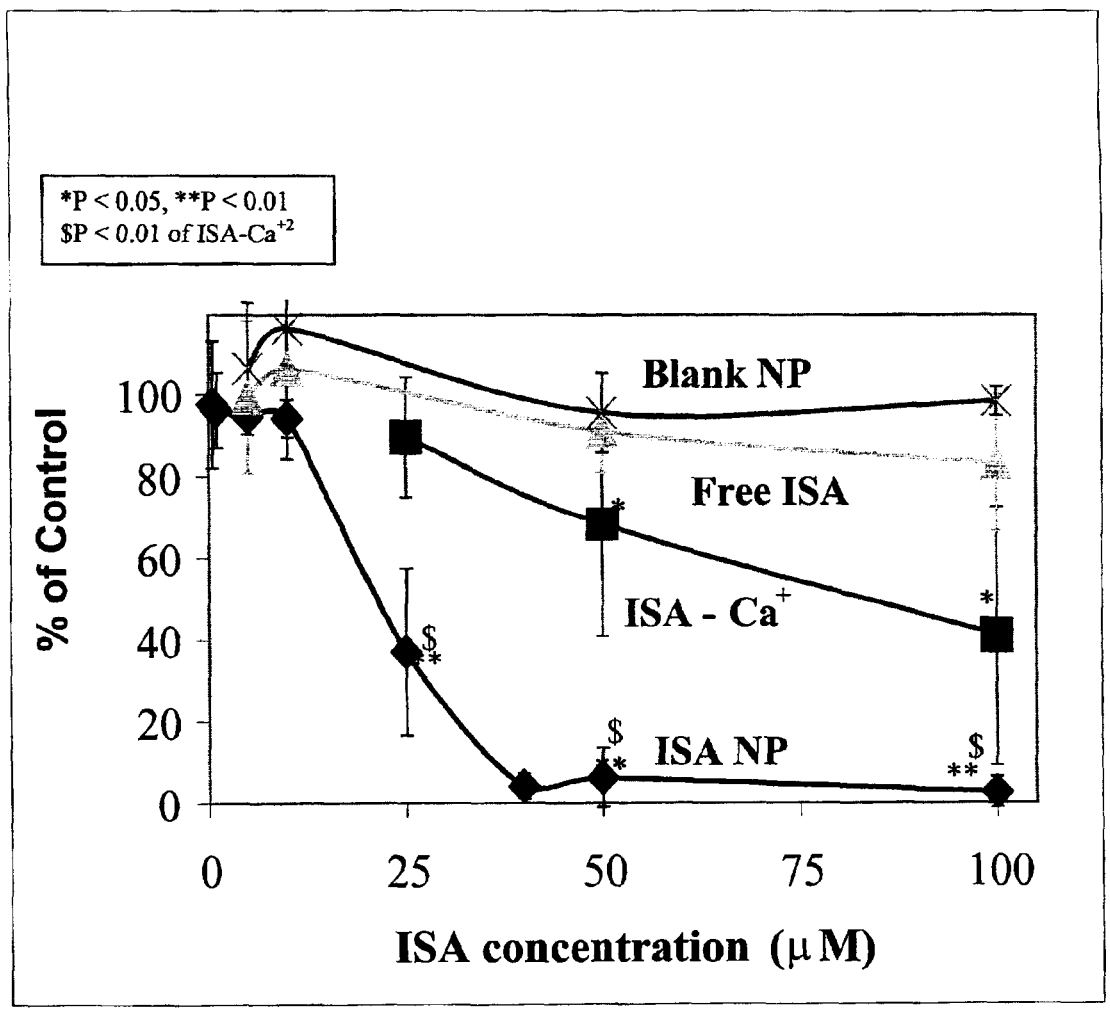
FIG. 6 illustrates the effect of ISA, specifically, free ISA, $Ca^{+2}$-ISA salt, and ISA encapsulated in nanoparticles, on the growth of RAW 264 cells in vitro.

The present invention relates to compositions and methods for reducing, delaying or eliminating restenosis. Reducing restenosis includes decreasing the thickening of the inner blood vessel lining that results from stimulation and proliferation of smooth muscle cell and other cell migration and proliferation, and from extracellular matrix accumulation, following various angioplasty procedures. Delaying restenosis includes delaying the time until angiographic re-narrowing of the vessel appears or until the onset of clinical symptoms which are attributed to stenosis of this vessel. Eliminating restenosis following angioplasty includes reducing hyperplasia to an extent which is less than 50% of the vascular lumen, with lack of clinical symptoms of restenosis. Methods of intervening include re-establishing a suitable blood flow through the vessel by methods such as, for example, repeat angioplasty and/or stent placement, or CABG.

The present invention includes a method of treating or preventing restenosis by administering to an individual, an effective amount of any compound or composite known to inactivate or inhibit blood monocytes and tissue macrophages.

One example of a group of drugs useful in the present invention to inhibit restenosis, are bisphosphonates ("BPs"). BPs inhibit smooth muscle cell migration and proliferation by transiently depleting and/or inactivating cells that are important triggers in the restenosis cascade, namely macrophages and/or monocytes. Bisphosphonates, when encapsulated in liposomes or nanoparticles in a "particle" dosage form, or when in a "free particulate" dosage form, such as, for example, in aggregates of a specific size, are taken-up, by way of phagocytosis, very efficiently by the macrophages and monocytes, and to some extent by other cells with phagocytic activity such as fibroblasts. Once inside the macrophages, the liposomal structure of the cell is disrupted and the bisphosphonates are released, thereby inhibiting the activity and/or killing the macrophages. Since macrophages, in their normal state, are recruited to the areas traumatized by angioplasty or other intrusive intervention and initiate the proliferation of smooth-muscle cells (SMC), inhibiting the macrophages' activity inhibits the migration and proliferation of SMC. Once released inside after being taken-up by the macrophages, the bisphosphonates have a sustained inhibitory activity on the macrophages. Thus, prolonged release of the bisphosphonates is not required in order to sustain inhibition. Accordingly, the method of inhibiting or reducing restenosis by administering a bisphosphonate in a particle or free particulate form is preferably a systemic therapy, in that the bisphosphonate particles and particulates target the circulating monocytes and macrophages.

It should be noted, however, that some bisphosphonate particles and particulates may have a direct effect on SMC activity. Additionally, some of the bisphosphonate particles and particulates may also inactivate other phagocytic cells and cells of the white-blood cell lineage in the body, such as liver and spleen macrophages and macrophages in the arterial walls.

Furthermore, the delivery system of the present invention not only retains the BP for a sufficient time so that the free BP is not released in the body fluids, but also efficiently discharges the drug within the cell. The free BP drug, as opposed to BP particles, is ineffective since it is not taken-up by phagocytic cells.

An additional example of a group of drugs useful in the present invention to inhibit restenosis are inactivators of monocytes/macrophages, such as gallium or gold.

In accordance with the present invention, a bisphosphonate or a compound or composite which inactivates monocytes/macrophages (collectively herein: "active ingredient") is used for treatment or prevention of vascular restenosis. The term bisphosphonate as used herein, denotes both geminal and non-geminal bisphosphonates. The term "active ingredient" encompasses in its scope, not only BP and compounds which inactivate monocytes/macrophage, but also polymeric chains of the BPs and the monocyte/macrophage inactivators, particularly such chains consisting of up to 40 BP monomers. Preferred active ingredients are compounds of the following formula (1)

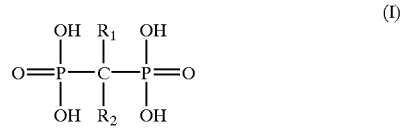

(I)

wherein $R_1$ is H, OH or a halogen atom; and
$R_2$ is halogen; linear or branched $C_1$–$C_{10}$ alkyl or $C_2$–$C_{10}$ alkenyl optionally substituted by heteroaryl or heterocyclyl $C_1$–$C_{10}$ alkylamino or $C_3$–$C_8$ cycloalkylamino where the amino may be a primary, secondary or tertiary; —NHY where Y is hydrogen, $C_3$–$C_8$ cycloalkyl, aryl or heteroaryl; or $R_2$ is —SZ where Z is chlorosubstituted phenyl or pyridinyl.

The present invention thus provides the use of said active ingredient, a complex of said active ingredient or a pharmaceutically acceptable salt or ester thereof for the preparation of a composition for the prevention or treatment of vascular restenosis. In one embodiment, the composition comprises a "particle" dosage form, wherein the active ingredient is encapsulated, embedded, and/or adsorbed within a particle, dispersed in the particle matrix, adsorbed or linked on the particle surface, or in combination of any of these forms. The particle includes any of the liposomes, microparticles, nanoparticles, nanospheres, microspheres, microcapsules, or nanocapsules known in the art (M. Donbrow in: Microencapsulation and Nanoparticles in Medicine and Pharmacy, CRC Press, Boca Raton, Fla., 347). The term particle includes both polymeric and non-polymeric preparations of the active ingredient. In a further embodiment, the composition comprises a "free particulate" dosage form of the active ingredient, such as an insoluble salt, insoluble ester, or insoluble complex of the active ingredient. Typically, "insoluble" refers to a solubility of one (1) part of a compound in more than ten-thousand (10,000) parts of a solvent. A "free particulate" dosage form includes any insoluble suspended or dispersed particulate form of the active ingredient which is not encapsulated, entrapped or adsorbed within a polymeric particle. Free particulates include, but are not limited to, suspended or dispersed colloids, aggregates, flocculates, insoluble salts and insoluble complexes. In yet a further embodiment, the composition comprises polymeric chains of the active ingredient. In a preferred embodiment, the composition comprises a bisphosphonate nanoparticle.

The present invention also provides a method of treatment of restenosis, comprising administering to an individual in need an effective amount of said active ingredient, a complex thereof or a pharmaceutically acceptable salt or ester thereof.

The present invention still further provides a pharmaceutical composition for the prevention or treatment of restenosis comprising, an effective amount of the active ingredient, a complex or a salt thereof, optionally together with a pharmaceutically acceptable carrier or diluent. Carriers include, but are not limited to, liposomes, particles, and lipid particles.

The term "effective amount" denotes an amount of the active ingredient, which is effective in achieving the desired therapeutic result, namely prevention, reduction, or elimination of vascular restenosis. The effective amount may depend on a number of factors including: weight and gender of the treated individual; the type of medical procedure, e.g. whether the vascular restenosis to be inhibited is following balloon angioplasty, balloon angioplasty followed by deployment of a stent; the mode of administration of the active ingredient (namely whether it is administered systemically or directly to the site); the type of carrier being used (e.g. whether it is a carrier that rapidly releases the active ingredient or a carrier that releases it over a period of time); the therapeutic regime (e.g. whether the active ingredient is administered once daily, several times a day, once every few days, or in a single dose); clinical factors influencing the rate of development of restenosis such as diabetes, smoking, hypercholesterolemia, renal diseases; anatomical factors such as whether there is severe preangioplasty stenosis, total occlusion, left anterior descending coronary artery location, saphenous vein graft lesion, long lesions, multivessel or multilesion PTCA; and on the dosage form of the composition. Moreover, procedural variables may also have bearing on the dosage, such as greater residual stenosis following PTCA, severe dissection, intimal tear, appropriate size of balloon, and the presence of thrombus. The artisan, by routine type experimentation should have no substantial difficulties in determining the effective amount in each case.

The invention is applicable for the prevention, reduction or treatment of vascular restenosis and mainly, but not limited to, coronary restenosis after angioplasty. Vascular restenosis primarily results from various angioplasty procedures including balloon angioplasty, intravascular stent deployment or other methods of percutaneous angioplasty (including angioplasty of coronary arteries, carotid arteries, and other vessels amenable for angioplasty) as well as for restenosis resulting from vascular graft stenosis (e.g. following by-pass surgery) (Braunwald, E., 1997, *Heart Disease* in: A textbook of cardiovascular medicine; 5th Ed., W. B. Saunders Company: Philadelphia).

In addition, the invention is also applicable for use in prevention, reduction or treatment of vascular restenosis in peripheral arteries and veins.

One exemplary application of the invention is to prevent and treat in-stent restenosis. It is a widely acceptable medical procedure to deploy a stent within a blood vessel within the framework of an angioplastic procedure, to support the walls of the blood vessel. However, very often restenosis occurs notwithstanding the presence of the stent within the blood vessel. In accordance with the invention, the above noted active ingredient may be administered, either systemically or directly to the site, in order to prevent or inhibit such restenosis. The active ingredient may be formulated in a manner allowing its incorporation onto the stent which, in fact, yields administration of said active ingredient directly at the site. The active ingredient may be formulated in that manner, for example, by including it within a coating of the stent. Examples of coatings are polymer coatings, (e.g., made of polyurethane), gels, fibrin gels, hydrogels, carbohydrates, gelatin, or any other biocompatible gel.

The active ingredient used in accordance with the invention may be formulated into pharmaceutical compositions by any of the conventional techniques known in the art (see for example, Alfonso, G. et al., 1995, in: The Science and Practice of Pharmacy, Mack Publishing, Easton Pa., 19th ed.). The compositions may be prepared in various forms suitable for injection, instillation or implantation in body such as suspensions of the nanoparticles, as in a coating of a medical device such as a stent (see above). In addition, the pharmaceutical compositions of the invention may be formulated with appropriate pharmaceutical additives for parental dosage forms. The preferred administration form in each case depends on the desired delivery mode, which is usually that which is the most physiologically compatible with the patient's condition and with the other therapeutic treatments which the patient currently receives.

In a preferred embodiment of the invention, the active ingredient is selected from the group of bisphosphonates. One preferred active ingredient for this group is the compound clodronate, (dichloromethylene) diphosphonic acid, (Fleisch, H., 1997, in: Bisphosphonates in bone disease. Parthenon Publishing Group Inc., 184–186) having the following formula (II):

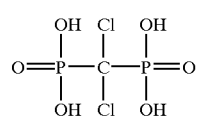
(II)

Clodronate was previously described for use in the treatment of hypercalcemia resulting from malignancy in the treatment of tumor associated osteolysis (Fleisch, H., 1997, in: Bisphosphonates in bone disease. Parthenon Publishing Group Inc., 184–186). Clodronate was also found to inhibit macrophages in vitro and to suppress macrophage activity in the spleen and liver tissues of mice. (Mönkkönen, J. et al, 1994, *J. Drug Target*, 2:299–308; Mönkkönen, J. et al., 1993, *Calcif. Tissue Int.*, 53:139–145).

Other preferred active ingredients of this group are etidronate and tiludronate having the following formulae (III) and (IV) respectively:

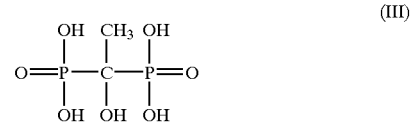
(III)

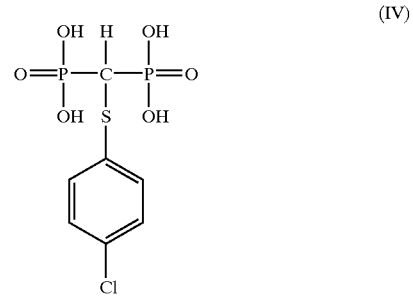
(IV)

Additional BPs having activities similar to that of clodronate are also preferred in accordance with the invention. Such BPs may be selected on the basis of their ability to mimic the biological activity of clodronate. This includes, for example: in vitro activity in inhibiting phagocytic activity of phagocytic cells, e.g. macrophages and fibroblasts; inhibition of secretion of IL-1 and/or IL-6 and/or TNF-α from macrophages; in vivo activity, e.g. the ability of the tested BP to prevent or reduce restenosis in an experimental animal model such as, for example, the rat or rabbit carotid catheter injury model described in Example 1 below, or porcine model of restenosis.

The most preferred group of active ingredients in accordance with the invention are the amino-BPs and any other nitrogen-containing BPs having the following general formula (V):

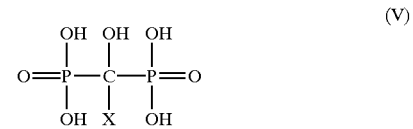
(V)

wherein X represents $C_1$–$C_{10}$ alkylamino or $C_3$–$C_8$ cycloalkylamino, where the amino may be primary, secondary or tertiary; or X represents NHY where Y is hydrogen, $C_3$–$C_8$ cycloalkyl, aryl or heteroaryl.

The BPs belonging to this group are believed not to be metabolized and have been shown at relatively low concentrations to induce secretion of the interleukin IL-1 and cause, at relatively high concentrations, apoptosis in macrophages (Mönkkönen, J. et al., 1993, *Calcif Tissue Int.*, 53:139–145). Preferred BPs belonging to this group are for example, pamidronate and alendronate having the following formulae (VI) and (VII), respectively.

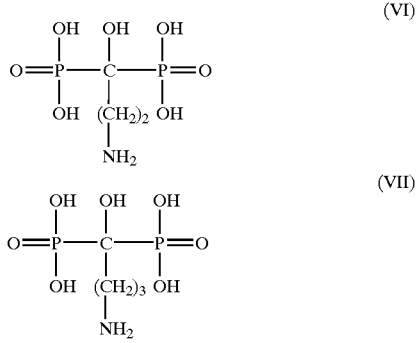

Although the geminal BPs are preferred BPs in accordance with the invention, non-geminal BPs, monophosphonates of BPs, termed generally as phosphonates may also be used as active ingredients in accordance with the invention.

Additional bisphosphonates include, but are not limited to, 3-(N,N-dimethylamino)-1-hydroxypropane-1,1-diphosphonic acid, e.g. dimethyl-APD; 1-hydroxy-ethylidene-1,1-bisphosphonic acid, e.g. etidronate; 1-hydroxy-3(methylpentylamino)-propylidene-bisphosphonic acid, (ibandronic acid), e.g. ibandronate; 6-amino-1-hydroxyhexane-1,1-diphosphonic acid, e.g. amino-hexyl-BP; 3-(N-methyl-N-pentylamino)-1-hydroxypropane-1,1-diphosphonic acid, e.g. methyl-pentyl-APD; 1-hydroxy-2-(imidazol-1-yl)ethane-1,1-diphosphonic acid, e.g. zoledronic acid; 1-hydroxy-2-(3-pyridyl)ethane-1,1-diphosphonic acid (risedronic acid), e.g. risedronate; 3-[N-(2-phenylthioethyl)-N-methylamino]-1-hydroxypropane-1,1-bishosphonic acid; 1-hydroxy-3-(pyrrolidin-1-yl)propane-1,1-bisphosphonic acid, 1-(N-phenylaminothiocarbonyl)methane-1,1-diphosphonic acid, e.g. FR 78844 (Fujisawa); 5-benzoyl-3,4-dihydro-2H-pyrazole-3,3-diphosphonic acid tetraethyl ester, e.g. U81581 (Upjohn); and 1-hydroxy-2-(imidazo[1,2-a]pyridin-3-yl)ethane-1,1-diphosphonic acid, e.g. YM 529.

Thus, suitable bisphosphonates for use in the present invention include the acid compounds presented above, any acceptable salts thereof, and crystalline and amorphous BPs. Additionally, the most preferred bisphosphonates are the amino-bisphosphonates such as alendronate, zolendronate, and risendronate.

The composition of the invention may comprise said active ingredient either encapsulated within a particle, adsorbed on the particle surface, complexed with metal cations such as calcium, magnesium or organic bases, formed into non-soluble salts or complexes, or polymerized to yield polymers of up to 40 monomers. The salts may be sodium, potassium, ammonium, gallium or calcium salts or salts formed with any other suitable cation (e.g. organic amino compounds). The salts or polymers may be in a micronized particulate form having a diameter within the range of about 0.01–1.0 μm, preferably within a range of about 0.1–0.5 μm. The active ingredients in their salt form may be with or without water of crystallization (hydrous and anhydrous). Additionally, additives such as polyvinyl alcohol (PVA), pluronics, and other surface active agents, may be used to stabilize the salt and or complex to establish a colloidal or nano-size suspension. In one embodiment for example, the composition may comprise a Ca-BP salt and or complex.

In one embodiment of the invention, the active ingredient is encapsulated in liposomes. The liposomes may be prepared by any of the methods known in the art (regarding liposome preparation methods see Mönkkönen, J. et al, 1994, *J. Drug Target*, 2:299–308, and Mönkkönen, J. et al., 1993, *Calcif. Tissue Int.*, 53:139–145). The liposomes may be positively charged, neutral or negatively charged (negatively charged liposomes being currently preferred), and may be single or multilamellar. Suitable liposomes in accordance with the invention are preferably non toxic liposomes such as, for example, those prepared from phosphatidyl-choline phosphoglycerol, and cholesterol, e.g. as described below. In many cases, use of liposomal delivery results in enhanced uptake of the active ingredient by cells not only via endocytosis but also via other pathways such as fusion (such uptake may play a role in the therapeutic effect). The diameter of the liposomes used may range from 0.15 to 300 nm. However, this is non-limiting, but merely an example, and liposomes of other size ranges may also be used.

In a preferred embodiment, the active ingredient or bisphosphonate may be encapsulated or embedded in inert particles. In a further embodiment, the active ingredient may be adsorbed onto the surface of, or adsorbed within, a blank particle, wherein a blank particle is a particle which has no drug encapsulated or embedded therein. Alternatively, the active ingredient may form a particulate, which includes a colloid, aggregate, flocculate or other such structure known in the art for the preparation of particulates of drugs. Furthermore, such particulates may be aggregates of the polymerized active ingredient.

Particulates of the active ingredient may be obtained by using an insoluble salt or complex that can be obtained in-situ, i.e., starting with the soluble drug and "salting-out" the drug by adding for example, Ca at the appropriate concentration and pH. The dispersed or free particulates are formed and then stabilized by the aid of surface active agents, suspending agents, deflocculating agents or by thickening agents, such those used in gels. The active ingredient may be further precipitated by adding a trivalent cation, for example, gallium, thereby forming a precipitate of gallium-BP salt/complex.

The active ingredient may be encapsulated within or adsorbed onto particles, e.g., nanoparticles by utilizing, for example, a modified nano-precipitation method. In this embodiment of the invention, the polymeric nanoparticle containing the active ingredient is formed by mixing water and organic solutions of the drug and polymer (PLGA or other polymers), respectively. Thus, the nanoparticle containing drug formed is suspended in water and can be lyophilized. Additionally, the active ingredient may be entrapped or adsorbed into blank polymeric nanoparticles, and/or adsorbed on the surface of the blank polymeric nanoparticles. (Blank nanoparticles are particles which have no drug encapsulated, embedded, and/or adsorbed therein).

One advantage of particulate dosage forms of the active ingredient itself, or of polymeric particle dosage forms (e.g. nanoparticles), is the possibility of lyophilization and of sterilization methods other than filter-sterilization. Thus, these forms of the active ingredient have an extended shelf-life and ease of handling.

In a preferred embodiment, the bisphosphonates may be encapsulated in nanoparticles ("NP"). Nanoparticles are 30–1000 nm diameter, spherical or non-spherical polymeric particles. The drug can be encapsulated in the nanoparticle, dispersed uniformly or non-uniformly in the polymer matrix (monolithic), adsorbed on the surface, or in combination of any of these forms. It is the submicron nature of this compositional form, which makes it more efficient in therapeutic applications. The submicron size facilitates uptake by phagocytic cells such as monocytes and macrophages, and avoids uptake in the lungs. In a preferred embodiment, the polymer used for fabricating nanoparticles is the biocompatible and biodegradable, poly(DL-lactide-co-glycolide) polymer (PLGA). However, any polymer which is biocompatible and biodegradable may be used. Therefore, additional polymers which may be used to fabricate the NP include, but are not limited to, polyanhydrides, polyalkylcyanoacrylates (such as polyisobutylcyanoacrylate), polyetheyleneglycols, polyethyleneoxides and their derivatives, chitosan, albumin, gelatin and the like. The size of the nanoparticle used to encapsulate the active ingredient or bisphosphonate depends on the method of preparation and the mode of administration (e.g. IV, IA, etc.) Preferably, the nanoparticles range in size from 70–500 nm. However, depending on preparation and sterilization techniques, the more preferred ranges include, but are not limited to, 100–300 nm and 100–220 nm.

Encapsulating a small, hydrophilic, and charged drug such as the bisphosphonate in a nanoparticle is described herein. During the preparation of the NP, there is a rapid diffusion of the drug into the water phase, thus resulting in a low entrapment efficiency. Accordingly, a formulation was developed to overcome this low encapsulation efficiency. The following formulation parameters may influence drug entrapment efficiency and release properties: buffers, emulsifiers, stabilizers such as PVA, amount and molecular weight of PLGA polymers, type of BP, non-solvent type, timing, rate of mixing and evaporation of the ingredients, vacuum, and temperature. A cation, such as $Ca^{+2}$, a non-solvent, or other compounds may be incorporated with the BP, prior to encapsulation with the nanoparticle, in order to reduce the solubility of the hydrophilic drug and increase its entrapment efficiency. A "non-solvent" is immiscible with the polymer or drug but is miscible with the other solvent present and, as such, forces the polymer or drug to leave its solvent. Several methods of nanoparticle preparation known in the art may be used; the common methods including, but not limited to, emulsion or double-emulsion solvent-evaporation precipitation methods, nanoprecipitation methods, coacervation methods, and solid-lipid liposomal methods.

Since the nanoparticles' surfaces are preferably negatively charged due to the acidic functional groups of the polymer and/or the BP, increased uptake by phagocytic cells is expected, thereby leading to increased activity against restenosis. Although particles which are neutral in charge may also be used to encapsulate the BPs, the most efficient uptake by the monocytes/macrophages occurs with charged particles, with negatively charged particles being preferred.

The pharmaceutical carrier or diluent used in the composition of the invention may be any one of the conventional solid or liquid or semisolid carriers known in the art. A solid carrier, for example, may be lactose, sucrose, gelatins, and other carbohydrates. A liquid carrier, for example, may be a biocompatible oil suitable for injection such as peanut oil, water or mixtures of biocompatible liquids, or a biocompatible viscous carrier such as a polyethylene or gelatin gel.

The composition of the active ingredient used for injection may be selected from emulsions, suspensions, colloidal solutions containing suitable additives, and additional suitable compositions known to the skilled artisan.

The compositions of the invention may be administered by any route which effectively transports the active compound to the appropriate or desirable site of action. By a preferred embodiment of the invention, the modes of administration are intravenous (IV) and intra-arterial (IA) (particularly suitable for on-line administration). Other suitable modes of administration include intramuscular (IM), subcutaneous (SC), or intraperitonal (IP). Such administration may be bolus injections or infusions. The compositions may also be administered locally to the diseased site of the artery, for example, by means of a medical device which is coated with the active ingredient. Another mode of administration may be by perivascular delivery. Combinations of any of the above routes of administration may also be used in accordance with the invention.

The dosage of the active ingredient to be used also depends on the specific activity of the active ingredient selected, on the mode of administration (e.g. systemic administration or local delivery), the form of the active ingredient (e.g. polymer, encapsulated in a particle such as a liposome, nanoparticle etc.), the size of the particle, and other factors as known per se.

In one embodiment, the dosage for alendronate in a PLGA nanoparticle preferably ranges from 0.015 mg/kg (per kg of body weight) to 3 mg/kg; more preferably, however, the dosage ranges from 0.15 to 1.5 mg/kg. Dosages outside these preferred ranges may also be used, as can be readily determined by the skilled artisan. When IV/IA injections or local delivery methods are used, i.e. via a balloon catheter, the dosage is at the lower end of the range. However, when IM or SC administration modes are used the dosage is approximately 10 times that used for IV administration.

In accordance with a preferred embodiment of the invention, treatment of an individual with the active ingredient may be for the purpose of preventing restenosis before its occurrence. For prevention, the active ingredient may be administered to the individual before angioplasty procedure, during the procedure or after the procedure as well as combination of before, during and after procedural administration. Furthermore, the active ingredient may be administered via IV, IA, IM, SC, IP or any other suitable type of administration. For example, the active ingredient may be administered via IA the day of the angioplasty procedure (day 0), via IV the day before the procedure (−1) and/or on day 0, or both via IV the day before the procedure (−1) and also after the procedural administration, for example, on day 6.

In accordance with a further embodiment of the invention, the active ingredient is administered to an individual suffering from restenosis for the purpose of reducing or treating restenosis. In such a case, the active ingredient may also be administered to the individual at different periods of time after restenosis is discovered, either alone or in combination with other kinds of treatments.

In addition, the active ingredient may be administered before any other conditions which may yield accelerated arteriosclerosis, as well as acutely after the process has begun to inhibit further development of the condition.

EXAMPLES

The invention will now be demonstrated by way of non-limiting examples with reference to the accompanying drawings. The animal models used in the examples below include the balloon-injured rat carotid arterial model and the balloon-injured hypercholesterolemic rabbit carotid arterial model. The rat is an acceptable model in evaluating the antirestenotic effects of drugs and composites; however, the rabbit is more preferred since it, unlike the rat, is both atherosclerotic and contains a significant number of macrophages in the arterial wall.

Example 1
Liposomes of Clodronate

Stock solutions of clodronate were prepared by dissolving the drug in deionized water at a concentration of 0.11 M, pH=7.

Liposome Preparation 38.9 mg of distearoylphosphatidylglycerol (DSPG), 118.5 mg of distearoyl-phosphatidylcholine (DSPC) and 38.7 mg of cholesterol were accurately weighed and dissolved in 20 ml of chloroform:methanol (9:1) in a round bottom vial. The vial was gently warmed, and the solvent was then evaporated in rotavapor. 20 mls of hydrated diisopropylether were then added and the vial was put into a water bath until the contents were dissolved. 8 mls of the clodronate solution prepared as described above were then added, and the solution was sonicated at 55° C. for a period of 45 minutes. The organic phase was then evaporated in rotavapor (55° C., 100 rpm). Similarly, other drug-containing liposomes can be prepared.

Purification of Prepared Liposomes

A Sephadex gel was prepared by dissolving 2.6 grams of Sephadex G-50 in 40 mls of water and stabilizing overnight. The column was rinsed with 100 mls of buffer (50 mM Mes +50 mM HEPES+75 mM NaCl, pH 7.2). The liposomes were applied to the column and the column was rinsed with the buffer. The liposome was seen as a band which can be followed in the column by its color. About 20 drops were collected from the column into each tube.

Animals

Animals were obtained and housed in the animal facilities of the Faculty of Medicine, The Hebrew University of Jerusalem, conforming to the standards for care and use of laboratory animals of the Hebrew University of Jerusalem. Male rats of Sabra strain weighing 350–420 g were used. The animals were fed standard laboratory chow and tap water ad libitum. All in vivo experiments were conducted under general anaesthesia achieved with 80 mg/kg ketamine and 5 mg/kg xylazine administered IP.

Rat Carotid Catheter Injury Model

The distal left common and external carotid arteries were exposed through a midline incision in the neck. The left common carotid artery was denuded of endothelium by the intraluminal passage of a 2F balloon catheter introduced through the external carotid artery. The catheter was passed three times with the balloon distended sufficiently with saline to generate a slight resistance. The catheter was then removed and the external carotid artery was ligated, and the wound was closed with surgical staples.

Seven rats served as the control group, and 6 rats as the treated group (randomly chosen). Liposomal clodronate was injected IV to the "treated group" one day prior to the arterial injury (6 mg of clodronate per rat) and repeated on day 6. In the control group similar injections were administered but with "empty" or blank liposomes (no clodronate).

All animals were sacrificed 14 days after injury by an overdose of pentobarbital. Arteries were perfusion-fixed with 150 ml of 4% formaldehyde solution pH 7.4 at 100 mm Hg. The right atrium was dissected and an 18G catheter connected to the perfusion system was inserted in the left ventricle. The arterial segments were dissected, cut, gently separated from the polymer, and postfixed for at least 48 hours in the same fixative solution. The arterial segments were embedded in paraffin and cut at 8–10 sites 600 $\mu$m apart. Sections of 6$\mu$m were then mounted and stained with Verhoeff's elastin stain for histologic examination.

Morphometric Analysis

The slides were examined microscopically by an investigator blinded to the type of the experimental group. Six to eight sections in each slide were evaluated by computerized morphometric analysis and the averaged section data were further used as a representative of a whole slide for comparisons between groups. The residual lumen, the area bounded by the internal elastic lamina (original lumen), and the area circumscribed by the external elastic lamina ("total arterial area") were measured directly. The degree of neointimal thickening was expressed as the ratio between the area of the neointimal and the original lumen (% stenosis), and as the ratio between the neointimal area to the area of the media (N/M). The medial area, an indirect index of SMC viability, was determined as the difference between the total arterial area and the original lumen area.

The surgical procedure and treatment did not cause mortality or apparent morbidity of the animals.

As seen in FIG. 1 the ratio between the neointimal area to the area of the media (N/M) was significantly reduced following treatment with clodronate-encapsulated in liposomes. The N/M ratio in clodronate treated rats was 0.28±0.23 as compared to 1.42±0.26 in the control group (mean±SD, p<0.01). Similarly as seen in FIG. 2, significant inhibition of % stenosis was achieved in the treated group: 9.8±7.76 vs. 41.53±7.9, treated and control groups, respectively (mean±SD, p<0.01). There were no apparent systemic side effects nor any effects on somatic growth as illustrated in FIG. 3.

Thus, the results of the experiments indicate that treatment of rats with clodronate-containing liposomes significantly reduces restenosis observed as neointimal formation following balloon-injury of the carotid artery.

Example 2

The antirestenotic effects of liposomal clodronate injections were studied in the balloon-injured rat and hypercholesterolemic rabbit carotid arterial models. The rats were treated by clodronate-containing liposomes, empty liposomes (control), and clodronate in solution (additional control). The dose of clodronate injected was 1.5 and 15 mg/kg administered one day before procedure (−1) and/or on day 6 (+6) post injury. The rabbits (following 30 days of atherosclerotic diet) were treated one day prior to balloon angioplasty by liposomal clodronate (10 mg/kg). The lumen, neointimal, medial and vessel areas and volumes were measured in the treated and control animal groups by digital planimetry of histological sections, at 14 and 30 days post injury in the rat and rabbit models, respectively.

The results of the antirestenotic effects of liposomal clodronate are shown in FIG. 4. As illustrated, no significant differences were found between treatments with empty liposomes, and free clodronate in solution, which both exhibited marked neointimal formation. The extent of mean neointimal formation, mean neointimal to media ratio (N/M), and % stenosis following treatment with clodronate-laden liposomes was significantly reduced. However, the medial area was not affected by the various treatments indicating no deleterious effects on quiescent cells. Moreover, there were neither apparent systemic side effects nor any effects on bone and somatic growth. Significantly, more potent treatments were evaluated, specifically, 1×15 mg/kg (−1) and 2×15 mg/kg (−1, and +6) injections, with no significant difference between them. Similar findings of no adverse effects were also observed in the rabbits' study. Liposomal clodronate was significantly effective in reducing neointimal formation and % stenosis.

Furthermore, injection of silica particles also reduces intimal formation (FIG. 4). This observation can be attributed to the known inhibiting effect of silica on macrophages.

The results of the experiment indicated that treatment by clodronate-containing liposomes significantly reduces neointimal formation following balloon-injury both in rat and rabbit models. There were neither apparent systemic nor local side effects nor any effects on somatic growth. It should be noted that although BPs are known as affecting bone, no effects on the bone or on calcium and phosphorus levels in bone and blood were observed following treatment with liposomal preparation of clodronate.

Example 3

Effect of ISA Composites on RAW 264 Proliferation

ISA Encapsulated in Nanoparticles

Nanoparticles (NP) were prepared by a novel solvent evaporation polymer precipitation technique using a double emulsion system. 20 mg of ISA acid (Cohen, H. et al., 1999, *Pharm. Res.*, 16: 1399–406) and 8.9 mg of $NaHCO_3$ were dissolved in 0.5 ml Tris buffer, and 90 mg of PLGA were dissolved in 3 ml dichloromethane. The aqueous sodium ISA solution was added to the PLGA organic solution and a water in oil (W/O) emulsion was formed by sonication over an ice-bath using a probe type sonicator. This W/O emulsion was then added to a 2% polyvinyl alcohol (PVA) (20 ml) filter sterilized solution, and the pH was adjusted to 7.4 with NaOH solution containing $CaCl_2$ in a molar ratio of 2:1 to ISA. The mixture was mixed over an ice bath, forming a double emulsion (W/O/W). The emulsion was stirred at 4° C. overnight to allow evaporation of the organic solvent.

Nanoparticles which did not have any drugs encapsulated within (termed blank NP) were prepared according to the same procedure by omitting the drug. $Ca^{+2}$-ISA salt with PVA and $Ca^{+2}$-ISA salt were prepared according to the same procedure by omitting the polymer or by omitting the polymer and the PVA, respectively. $Ca^{+2}$-ISA was adsorbed on blank naoparticles (prepared as above) by dispersing the nanoparticles in the buffer and precipitating ISA-calcium with the same ingredients as used above. The amount of drug entrapped in the NPs was determined spectrophotometerically following sequential ultracentrifugation.

The influence of various formulation parameters on drug entrapment efficiency, release properties, and size have been examined. For example, the following parameters were evaluated: buffers, emulsifiers, various amounts of ISA, $CaCl_2$ (including without), amount of PVA (including without), different amounts and molecular weights of PLGA/PLA polymers, temperature, yield and extrament efficiency. The various formulation steps resulted in the development of spherical nanoparticles containing ISA. Furthermore, NP formulation reproducibility was successfully demonstrated. High yield, entrapment efficiency, as well as lyophilizability are important features for any nanoparticulate carrier.

FIG. 5 tabulates typical formulations of both ISA loaded nanoparticles and blank nanoparticles. Whereas FIG. 5 illustrates a typical formulation, it shall be understood that additional formulations may also be effective. The formulation parameters tabulated include the size of the nanoparticle both before and after lyophilization, the percent recovery, the ISA entrapment (measuered as % of initial), the final ISA content, the ISA in NP, the ISA in the supernatant, the initial ISA content, the $Ca^{+2}$ recovery, the $Ca^{+2}$ in the supernatant, the $Ca^{+2}$ in NP, the ratio of $Ca^{+2}$ to ISA, and the Zeta potential. The size of the nanoparticle before lyophilization was 376 nm and increased 396 nm after lyophilization. Typically, the size of the nanoparticles range from 100–500 $\mu$m, depending not only upon preparation and sterilization techniques, but also upon the mode of administration. Lyophilization not only increases the shelf-life of the nanoparticles, but also enables steriliztion of the NP through irradiation. The percent recovery is tabulated in FIG. 5 as 68.7%. Essential to the antirestenotic effect of the bisphosphonate NP is the bisphophonate content within the nanoparticle and the entrapment efficiency. These parameters are measured by: ISA entrampment, tabulated in FIG. 5 as 59.6%; final ISA content, measured as the ratio between ISA weight over the NP total weight, and tabulated as 16.5%, but may range from 25to 40%; the amount of ISA in NP, tabulated as 11.9 mg, but may be changed accordingly; the amount of ISA in the supernatant tabulated as 1.1 mg, but may range as a function of the entrapment efficiency mentioned above; and the initial ISA content, tabulated as 18.1%, but may be any percentage in an appropriate ratio to the polymer amount. In order to reduce the solubility of the hydrophilic drug and increase its entrapment efficiency, a cation, such as $Ca^{+2}$ is added to the composite. The parameters associated with $Ca^{+2}$ include: $Ca^{+2}$ recovery, tabulated as 72.3%; $Ca^{+2}$ in supernatant, tabulated as 38%; $Ca^{+2}$ in NP, tabulated as 34%; and $Ca^{+2}$/ISA, tabulated as 1.2 mols. However, these parameters may range as a function of the ratio between calcium to ISA, the type of additives, the pH of solution and other like factors. Additionally, the Zeta potential is tabulated as −5.7. A negative value for the nanoparticle zeta potential is important for efficient uptake by phagocytic cells (e.g. macrophages).

Furthermore, lyophilized NPs were shown to have similar properties to non-lyophilized NPs, in both in vitro and in vivo experiments. Indeed, this is of significant importance since NP sterilization could be obtained through γ irradiation of dry NP, ethylene-oxide sterilization, steam sterilization (when other polymers are used) or filter sterilization.

Each particle carrier (e.g., polymeric micro/nanoparticle) exhibited a certain entrapment efficiency for the bisphosphonate drug. The ISA entrapment efficiency in the NP reached 60% and is substantially higher than any efficiency that is reported in the literature for any given hydrophilic drug in either PLGA nanoparticles or liposomes.

The bisphosphonate, ISA, serves as a model bisphosphonate. The physicochemical properties of other BPs are similar to those of ISA. Moreover, ISA serves as model drug for a low molecular weight, hydrophilic, charged molecule and, as such, was used as a model bisphosphonate in the experiments herein. For properties of ISA, refer to, Cohen H, Alferiev I S, Monkkonen J, Seibel M J, Pinto T, Ezra A, Solomon V, Stepensky D, Sagi H, Ornoy A, Patlas N, Hagele G, Hoffman A, Breuer E, Golomb G, 1999, "Synthesis and preclinical pharmacology of 2-(2-aminopyrimidinio) ethylidene-1,1-bisphosphonic acid betaine (ISA-13-1)-a novel bisphosphonate." *Pharm Res.*; 16:1399–406.

In vitro Bioactivity

The effect of ISA on the growth of RAW 264 cells was determined. RAW 264 cells, which are derived from the murine macrophage cell lines, were plated at $2 \times 10^4$ cells per well in 24-well plates and allowed to grow for approximately 24 hours in DMEM. The cells were then treated with various compositions of the ISA drug, specifically, free ISA, the ISA–$Ca^{+2}$ salt, and ISA encapsulated in a nanoparticle ("ISA NP"). As discussed supra, the ISA NP contains $Ca^{+2}$ to lower the solubility of the bisphosphonate and increase its entrapment efficiency. For comparison purposes, the RAW 264 cells were also treated with blank NP, i.e., nanoparticles with no drug embedded therein. The cells were then analyzed 48 hours after treatment. Analysis included cell counting by Coulter counter and cell viability by tryphan blue exclusion assay.

The effect of ISA compositions on the growth of RAW 264 cells in vitro is illustrated in FIG. 6. The cell proliferation in buffer only was termed as 100%. The data represented is the mean with a ±SD ($6 \leq N \leq 27$). As the legend designates, *P<0.05, **P<0.01 in comparison to buffer and $ P<0.01 in comparison to ISA+$Ca^{+2}$ indicating that the differences are statistically significant.

As depicted in FIG. 6, free ISA had only a minor effect on the growth of RAW 264 cells (macrophages). However, the addition of equal $Ca^{+2}$ concentrations to ISA to form a salt, potentiated the bishposphonates activity, and significantly suppressed the proliferation of RAW 264 cells in a dose response manner. Indeed, the use of ISA–$Ca^{+2}$ salt served as an appropriate control group to ISA NP activities since both compositions contained equivalent molar amounts of $Ca^{+2}$ and ISA. ISA encapsulated in nanoparticles ("ISA NP") were found to be potent inhibitors of the growth of RAW 264 cells. As illustrated in FIG. 6, the ISA NP were far more potent than both ISA and ISA+$Ca^{+2}$. The blank NP had no effect on the proliferation of RAW 264 cells up to 100 $\mu$M, indicating that the ISA NP growth inhibitory effect was caused by ISA and not by the polymer.

Figure 7:
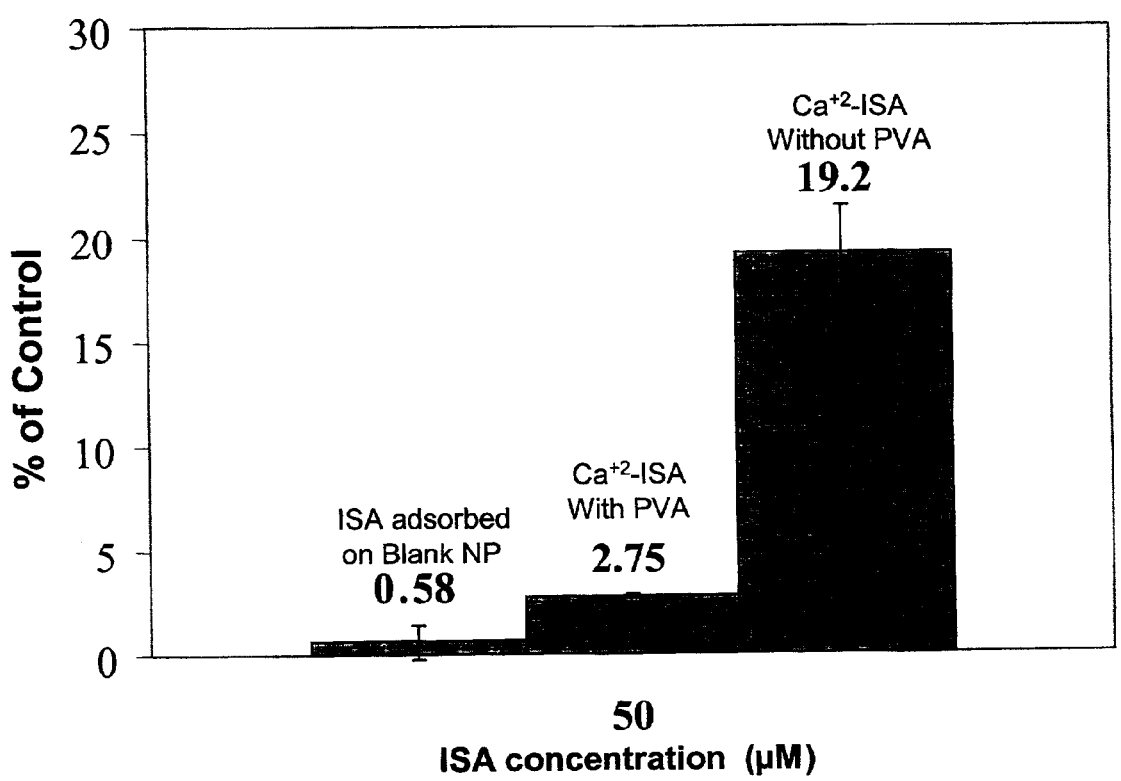
FIG. 7 illustrates the effect of 50 $\mu$M $Ca^{+2}$-ISA salt formulations, specifically, $Ca^2$-ISA adsorbed on blank NP, $Ca^{+2}$-ISA salt and polyvinyl alcohol (PVA), and $Ca^{+2}$-ISA salt, on the proliferation of RAW 264 cells in vitro.

Additionally, the effect of $Ca^{+2}$-ISA salt formulations on RAW 264 proliferation is presented in FIG. 7. The following formulations were evaluated: $Ca^{+2}$-ISA salt, $Ca^{+2}$-ISA salt+PVA, and $Ca^{+2}$-ISA adsorbed on the surface of a blank NP. The cell proliferation in the buffer only was termed as 100%. N.B., a lower column represents higher potency.

As depicted in FIG. 7, $Ca^{+2}$-ISA salt potently inhibited the proliferation of RAW 264 cells at 50 $\mu$M, and the addition of PVA to $Ca^{+2}$-ISA salt further potentiated its activity. As discussed supra, PVA is an additive which is used to stabilize the BP-salt/complex. However, $Ca^{+2}$-ISA adsorbed on the surface of the blank NP significantly suppressed RAW 264 cell proliferation. As illustrated in FIGS. 6 and 7, the $Ca^{+2}$-ISA salt (50 $\mu$M) adsorbed on a blank NP and ISA encapsulated in NP (50 $\mu$M) were comparable inhibitors of RAW 264 proliferation. In summary, the results of the experiment indicate that $Ca^{+2}$-ISA salt particulates are useful in inhibiting restenosis by eliminating or inhibiting macrophages.

However, in vivo utilization of $Ca^{+2}$-ISA salt particulates to eliminate macrophages, requires maintaining the composites in the nanometer size in order to be suitable for IV use. Maintaining the salt composites in the nanometer size may be achieved with a proper surfactant during the $Ca^{+2}$-ISA salt preparation. Indeed, the benefit of utilizing a $Ca^{+2}$-ISA salt composite to treat restenosis is its simplicity and the avoidance of PLGA use. However, a possible drawback of this approach might be the rapid dissolution of the $Ca^{+2}$-ISA salt seconds after administration, due to high dilution.

Similar experiments were conducted to determine the effect of ISA NP on the proliferation of smooth muscle cells extracted from the aortas of adult male Sabra rats and 3T3 fibroblast cells. The results of the experiment (not shown) indicate that ISA NP significantly inhibited the growth of rat SMC and 3T3 cells (fibroblasts).

In summary, ISA encapsulated within NP was found to inhibit the growth of the three main cell types involved in the restenotic cascade, namely macrophages (RAW 264 cells), fibroblasts (3T3 cells) and smooth-muscle cells (SMC).

Example 4

Effect of ISA-Nanoparticles Rat Carotid Model of Restenosis

In vivo Bioactivity

The following experiment examined the effect of ISA encapsulated in NP, specifically PLGA based NP, on neointimal formation. The ISA NP were prepared as described supra, in Example 3. Additionally, Male Sabra rats were used and prepared according to the rat carotid catheter injury model described supra, in Example 1. ISA NP was injected IV to the "treated group" one day prior to the arterial injury (–1d) at a dosage of 15 mg/kg. In the control group, similar injections were administered but with blank NP, i.e. nanoparticles with no ISA encapsulated or adsorbed therein.

The animals were then sacrificed 14 days of injury, their arterial segments dissected and prepared for histologic examination. (Refer supra, in Example 1, for details). The arterial segments were evaluated by computerized morphometric analysis. The residual lumen, the area bounded by the internal elastic lamina (original lumen), and the area circumscribed by the external elastic lamina (total arterial area) were measured directly. The degree of neointimal thickening was expressed as the ratio between the area of the neointimal and the original lumen (% stenosis), and as the ratio between the neointimal area to the area of the media (N/M). The medial area, an indirect index of SMC viability, was determined as the difference between the total arterial area and the original lumen area.

Figure 8A:
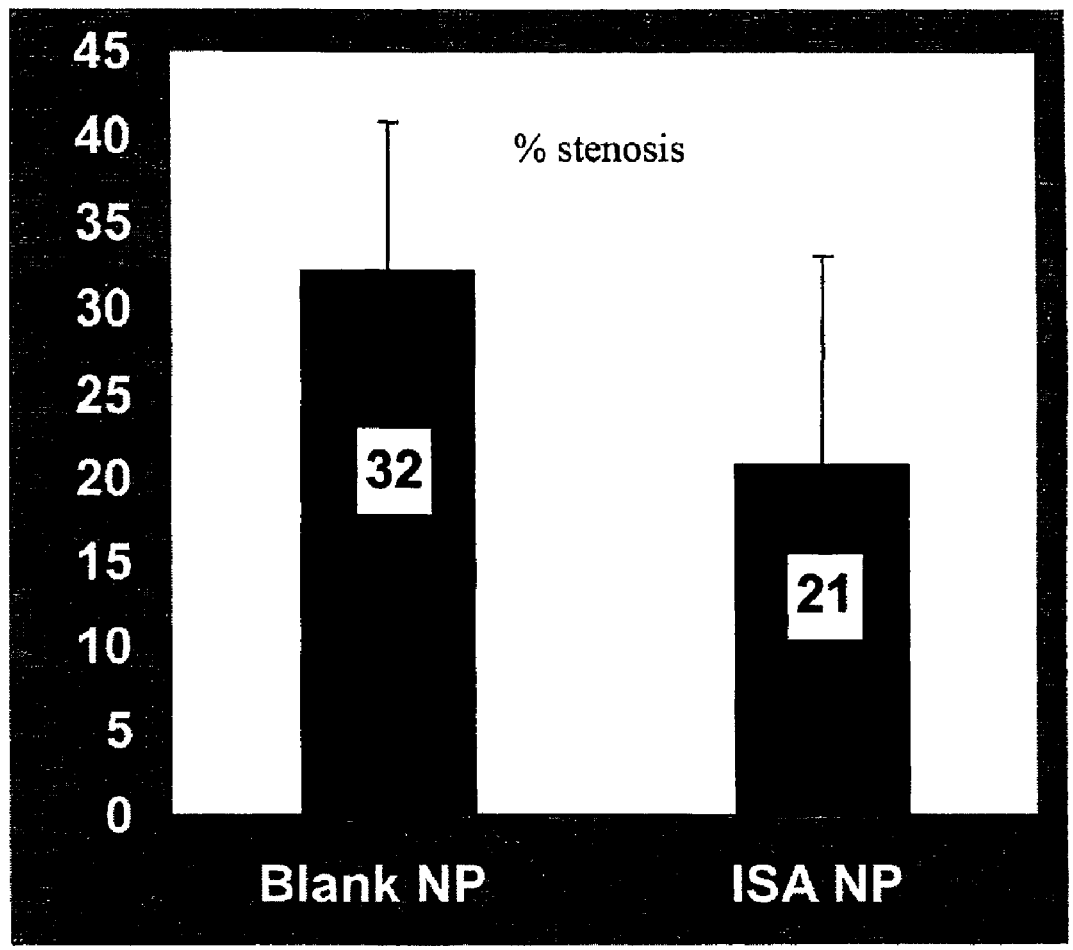
FIGS. 8a and 8b are bar graphs of results demonstrating the effect of ISA encapsulated in nanoparticles on the reduction of restenosis in an experimental rat carotid catheter injury model as compared to the effect of control nanoparticles (i.e., blank NP) which did not contain ISA, on the same rats. In these figures.
Figure 8B:
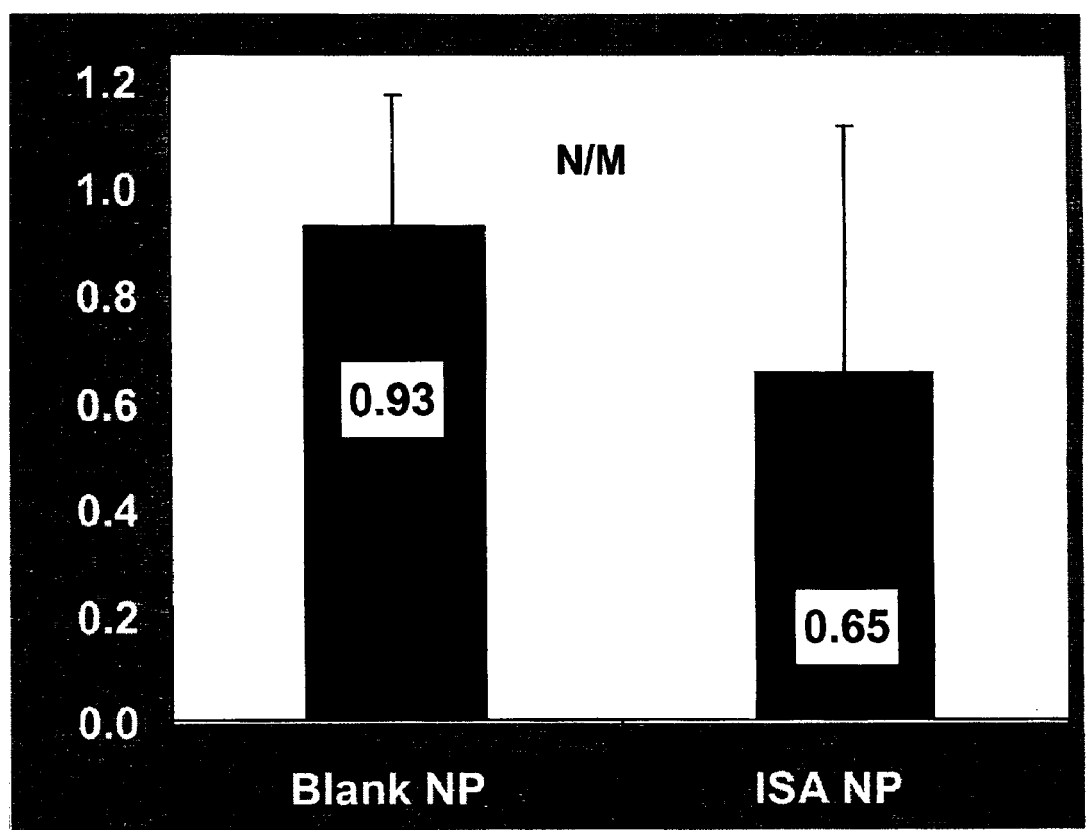

The experimental results indicate that administration of ISA NP significantly inhibited vascular neointimal formation in comparison to blank NP treatment. As indicated in FIG. 8A, significant inhibition of % stenosis was achieved in the ISA NP treated group (n=12). Similarly, as illustrated in FIG. 8B, the extent of mean neointimal formation and mean neointimal to media ratio (N/M) following treatment with ISA NP was significantly reduced. Thus, the experimental results indicate that treatment of rats with ISA encapuslated nanoparticles via IV administration significantly reduces restenosis observed as neointimal formation following balloon-injury of the carotid artery.

Additionally, SC administration of ISA encapsulated in nanoparticles was evaluated and found to significantly inhibit neointimal formation 14 days after vascular injury. However, the SC administration provided a weaker restenosis inhibiting effect than that obtained from IV delivery of the ISA NP.

In summary, the above experiments indicate that the improved stability, high drug entrapment efficiency, and increased bioactivity of ISA encapsulated in NP or ISA absorbed on NP, possess novel and important advantages for clinical applications. Additionally, Ca-BP salt particulates were also found to be bioactive and effective in inhibiting proliferation of monocytes.

Example 5

Effect of Alendronate-Nanoparticles in Rabbit Model of Restenosis

Alendronate NPs

Alendronate encapsulated within nanoparticles ("alendronate NPs") were prepared by a novel solvent evaporation polymer precipitation technique using a double emulsion system. 20 mg of alendronate were dissolved in 0.5 ml Tris buffer with 2.8% PVA and 90 mg of PLGA were dissolved in 3 ml dichloromethane. The aqueous alendronate solution was added to PLGA organic solution and a water in oil (W/O) emulsion was formed by sonication over an ice bath using a probe type sonicator, at 14 W for 90 seconds. This W/O emulsion was further added to 10.5 ml of Tris buffer (containing 2% PVA and $CaCl_2$ solution in molar ratio 2:1 to alendronate), and sonicated for 90 seconds over an ice bath, forming the double emulsion (W/O/W). The emulsion was stirred at 4° C. for 3 hours, to allow evaporation of the organic solvent.

FIG. 9 tabulates the formulation parameters for the alendronate NP formed. Although FIG. 9 tabulates a typical alendronate NP, it shall be understood that various formulations may also be effective. The formulation parameters include size, alendronate entrapment, the amount of alendronate in NP, the alendronate in supernatant, the initial amount of alendronate, the PLGA amount and the volume of a 0.246M calcium chloride solution. The size of the nanoparticle was 219 nm. As discussed supra, typically, the size of the nanoparticles range from 100–500 nm, depending not only upon preparation and sterilization techniques, but also upon the mode of administration. Essential to the antirestenotic effect of the bisphosphonate NP is the bisphophonate content within the nanoparticle and the entrapment efficiency. These parameters are measured by: alendronate entrapment, tabulated in FIG. 9 as 55.1%; alendronate in NP, tabulated as 1.002 mg/ml; alendronate in the supernatant, tabulated as 0.232 mg/ml; the initial amount of alendronate, tabulated as 20 mg; the PLGA amount, tabulated as 90 mg; and the volume of calcium chloride, tabulated as 0.5 ml. However, these parameters may be modified to provide additional formulations. In the experiment, the effect of alendronate NP on RAW 264 proliferation was evaluated. For procedures describing the growth of RAW 264 cells and subsequent treatment with NP refer to Example 3, supra. As depicted in FIG. 10, alendronate NP are potent inhibitors of macrophages, whose activity increases with concentration.

Balloon-injured Hypercholesterolemic Rabbit Arterial Model

The antirestenotic effect of alendronate NPs was evaluated in both the balloon-injured rat and the balloon-injured hypercholesterolemic rabbit carotid arterial models. While alendronate NPs were successful in reducing restenosis in both models, of significant importance is the marked efficacy discovered in the hypercholesterolemic model of balloon-injured rabbits. The rabbits were treated by alendronate NPs and blank NPs (control) via SC and IV administration in order to compare the differences between the two modes of administration. A group of rabbits were treated one day prior to balloon angioplasty with 1.5 mg/kg of alendronate NPs via SC administration. For comparison purposes, two additional groups were also treated one day before the procedure (−1d) with 0.15 mg/kg of alendronate NPs via SC and IV administration. The lumen, neointimal, medial and vessel areas were measured in the treated and control rabbit groups by digital planimetry of histological sections at 30 days post injury.

Figure 11:
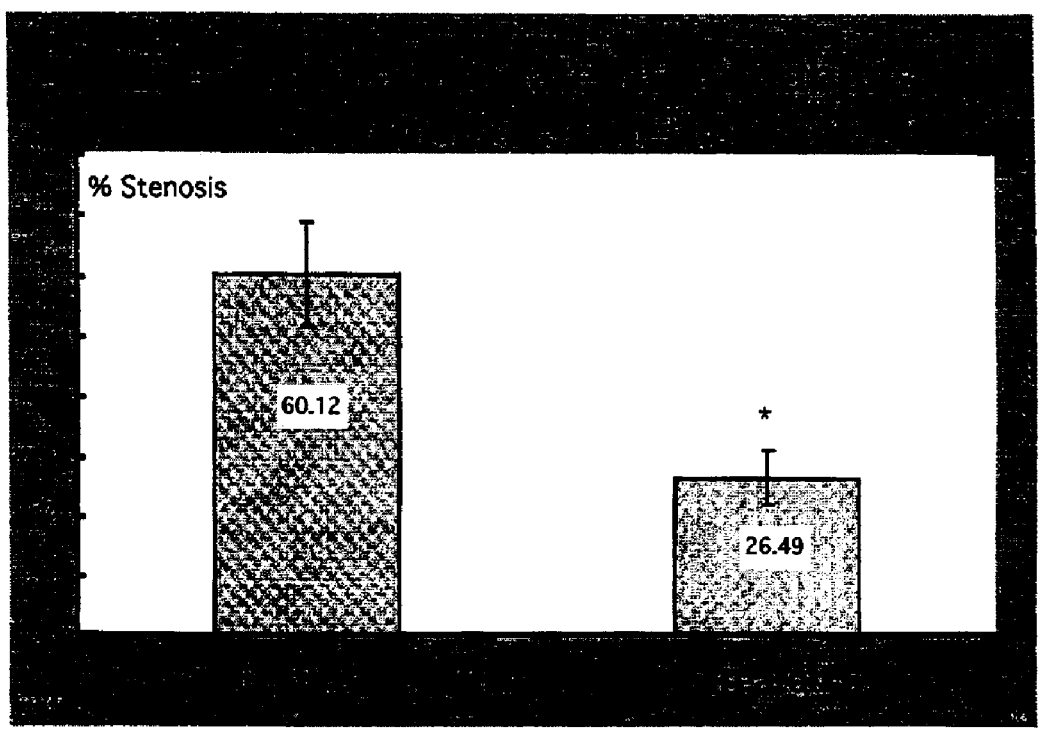
FIGS. 11, 12a and 12b are bar graphs of results demonstrating the effect of alendronate encapsulated in nanoparticles on the reduction of restenosis in a hypercholesterolemic balloon-injured rabbit model as compared to the effect of control nanoparticles which did not contain alendronate on the same rats via subcutaneous administration. The graphs also compare the effect of subcutaneous (SC) and intravenous (IV) administration in reducing restenosis. In these figures.
Figure 12A:
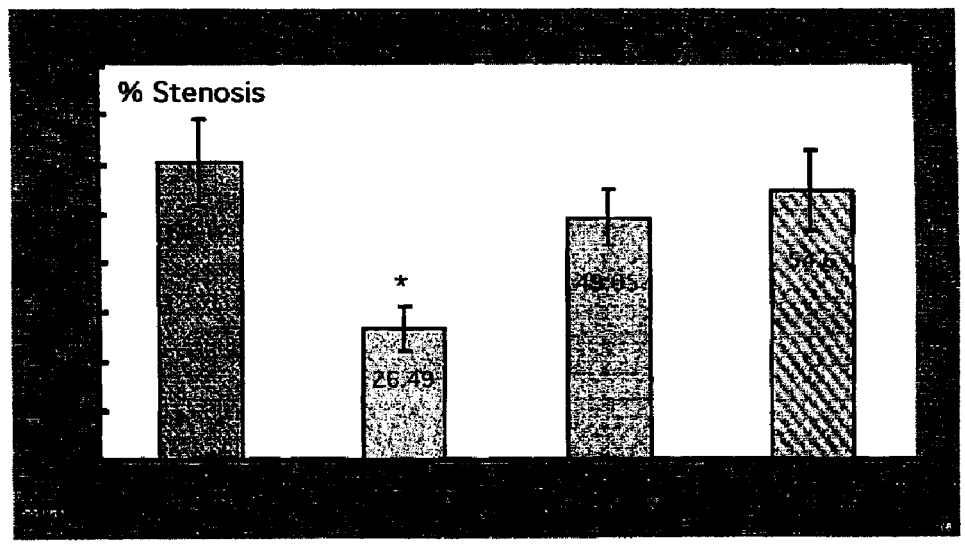
Figure 12B:
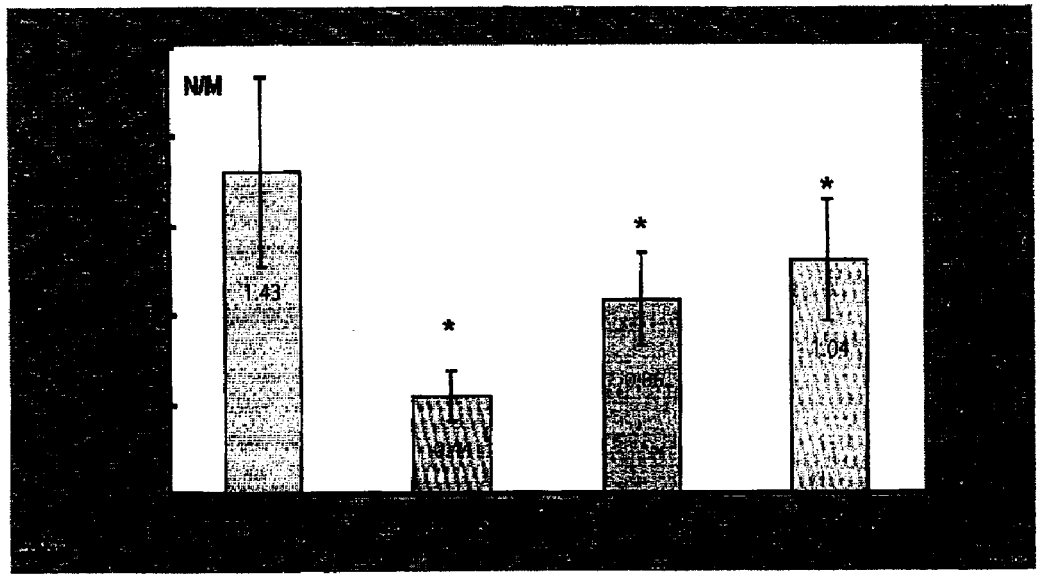

The results of the antirestenotic effects of alendronate NPs in the balloon-injured hypercholesterolemic rabbit model are illustrated in FIGS. 11, 12a and 12b.

FIG. 11 illustrates that the % restenosis following treatment with alendronate NPs via SC administration was significantly reduced.

FIGS. 12a and 12b compare the effect of two dosage amounts of the alendronate NPs via SC administration, specifically 1.5 and 0.15 mg/kg and also the effects of two modes of administration, IV and SC. As illustrated in the figures, the mean neointimal to media ratio (N/M) and % stenosis was reduced in a dose response manner. Specifically, a dose of 1.5 mg/kg was more effective in reducing N/M and % restenosis in comparison to 0.15 mg/kg. Moreover, the inhibition of neointimal formation and % restenosis by alendronate NPs via SC administration was slightly greater than that obtained via IV delivery, although not significant in light of the experimental standard deviation. Additionally, there were neither apparent systemic side effects nor any effects on bone and somatic growth.

In conclusion, alendronate NP is a highly potent inhibitor of restenosis in animal models via SC and IV administration. Furthermore, the dosage range of 0.15 to 1.5 mg/kg was found to be the most potent delivery system in preventing restenosis.

Example 6

Effect of Alendronate-Nanoparticles in Human Blood

In this example, the ability of alendronate NPs to decrease the number of monocytes in human blood was studied. Human blood was drawn to EDTA-containing test tubes and 200 µl were incubated for 24 h in 37° C. on a shaker with the indicated doses of alendronate-nanoparticles in 50 µl diluted in 50 of PBS. Control samples were incubated with 50 µl. The samples were then incubated (30 min. 4° C., in the dark) with RPE-conjugated anti-CD14 Ab (specific for monocytes) for 30 min. RBC (red blood cells) were lysed by FACS lysing solution (Becton-Dickinson, San-Jose, Calif.) and distilled water, and following washings in FACS (fluorescence activated cell sorting) solution, flow cytometry analysis was performed. Monocytes were detected by side-scattering and fluorescence.

Figure 13:
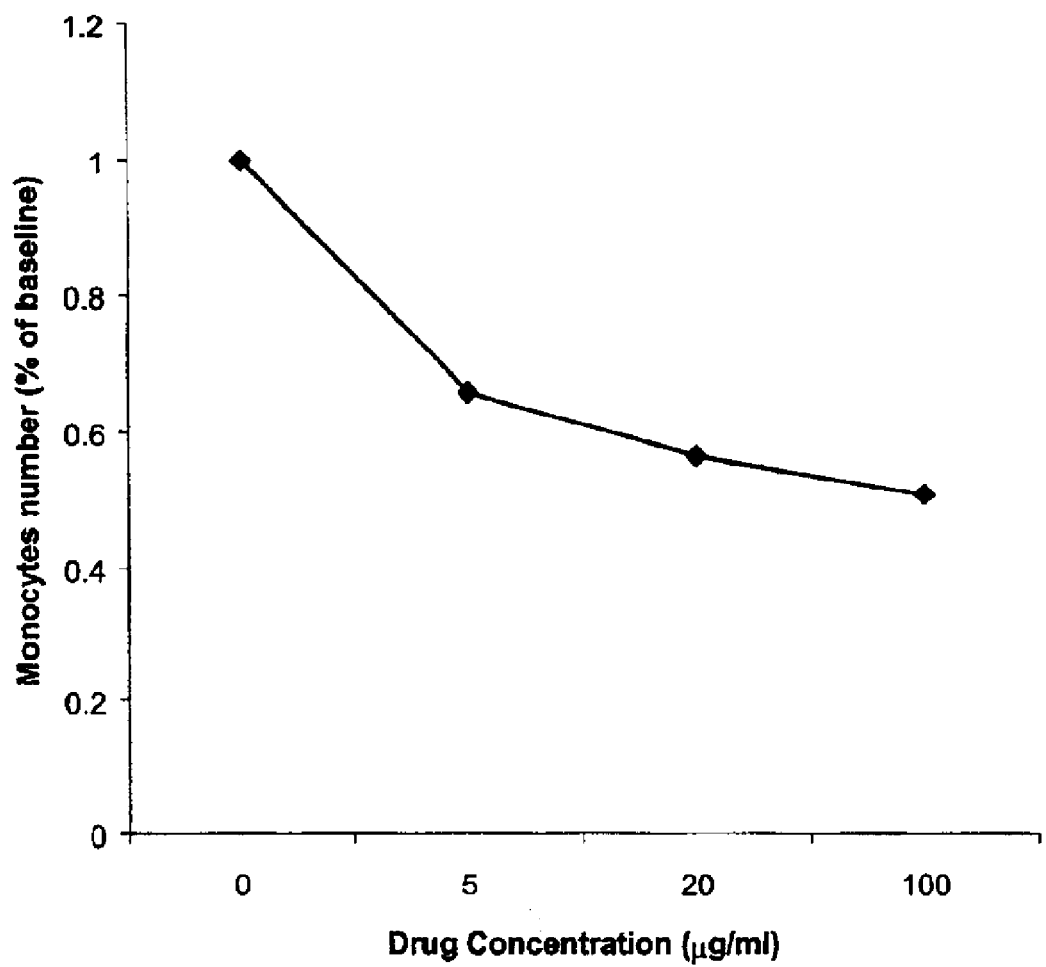
FIG. 13 illustrates the effect of alendronate encapsulated in nanoparticles on the number of monocytes in the human blood following incubation for 24 hours.

The results of the anti-proliferative effects of alendronate-nanoparticles on monocytes in human blood are illustrated in FIG. 13. It is apparent that alendronate NPs potently decreased the amount of monocytes in human blood in a dose response manner. Since monocytes, in their normal state, are recruited to the areas traumatized by angioplasty or other intrusive intervention and initiate the proliferation of smooth-muscle cells, thus leading to restenosis, inhibiting the number of monocytes will inhibit restenosis.

We claim:

1. A method of treating or inhibiting restenosis comprising administering to an individual in need thereof an effective amount of an active ingredient selected from the group consisting of a bisphosphonate, a bisphosphonate salt, a bisphosphonate ester, and a bisphosphonate complex, wherein the active ingredient is encapsulated in, embedded in, absorbed onto, or linked to a particle having a size of 0.03–1.0 microns.

2. A method of treating or inhibiting restenosis, comprising administering to an individual in need thereof an effective amount of an active ingredient selected from the group consisting of a bisphosphonate, biaphosphonate salt, bisphosphonate ester, and bisphosphonate complex, wherein the active ingredient has been formulated into an insoluble particulate having a size of 0.01–1.0 microns.

3. The method according to claim 1, wherein the particle is selected from the group consisting of polymeric particles, liposomes, microparticles, nanoparticles, microspheres, and nanospheres.

4. The method according to claim 2, wherein the particulate is selected from the group consisting of aggregates, flocculates, colloids, polymer chains, insoluble salts, insoluble esters, and insoluble complexes.

5. The method according to claim 1, wherein the active ingredient is encapsulated within the particle.

6. The method according to claim 1, wherein the active ingredient is embedded within the particle.

7. The method according to claim 1, wherein the active ingredient is adsorbed on a surface of the particle.

8. The method according to claim 1 or 2, wherein said bisphosphonate has the following formula (I):

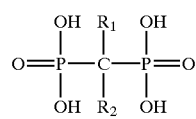
(I)

wherein $R_1$ is H, OH or a halogen atom; and $R_2$ is a halogen; linear or branched $C_1$–$C_{10}$ alkyl or $C_2$–$C_{10}$ alkenyl optionally substituted by heteroaryl or heterocyclyl $C_1$–$C_{10}$ alkylamino or $C_3$–$C_8$ cycloalkylamino where the amino may be a primary, secondary or tertiary; —NHY where Y is hydrogen, $C_3$–$C_8$ cycloalkyl, aryl or heteroaryl; or $R_2$ is —SZ where Z is chlorosubstituted phenyl or pyridinyl.

9. The method according to claim 1 or 2, wherein said bisphosphonate is clodronate, etidronate, tiludronate, pamidronate, alendronate, risendronate or ISA.

10. The method according to claim 1 or 2, wherein the administering is intravenous (IV), intrarterial (IA), intramuscular (IM), subcutaneous (SC), intraperitoneal (IP), or delivered by a 'sweating balloon', a coated balloon or on a coated stent.

11. The method according to claim 1 or 2, wherein the particle or particulate is administered before an angioplasty procedure.

12. The method according to claim 1 or 2, wherein the particle or particulate is administered the day of an angioplasty procedure.

13. The method according to claim 1 or 2, wherein the particle or particulate is administered after an angioplasty procedure.

14. A method of treating or inhibiting restenosis comprising administering to an individual in need thereof an effective amount of a bisphosphonate encapsulated in, embedded in, absorbed onto, or linked to a nanoparticle having a size of 0.03–1.0 microns.

* * * * *